(12) United States Patent
Kim et al.

(10) Patent No.: US 8,446,583 B2
(45) Date of Patent: May 21, 2013

(54) LIGHT FOCUSING UNIT AND SPECTRUM MEASURING APPARATUS HAVING THE SAME

(75) Inventors: Hyun-Jong Kim, Hwaseong-si (KR); Chung-Sam Jun, Suwon-si (KR); Hwan-Shik Park, Seoul (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 381 days.

(21) Appl. No.: 12/662,650

(22) Filed: Apr. 27, 2010

(65) Prior Publication Data

US 2010/0277729 A1    Nov. 4, 2010

(30) Foreign Application Priority Data

Apr. 30, 2009 (KR) .................. 10-2009-0038399

(51) Int. Cl.
*G01J 4/00* (2006.01)
(52) U.S. Cl.
USPC ............................ 356/369; 356/364; 356/327
(58) Field of Classification Search
USPC ............................ 356/364, 369, 327; 359/365
See application file for complete search history.

(56) References Cited

U.S. PATENT DOCUMENTS

| | | | | |
|---|---|---|---|---|
| 5,166,752 A * | 11/1992 | Spanier et al. | ................. | 356/369 |
| 5,889,593 A * | 3/1999 | Bareket | .......................... | 356/445 |
| 6,002,485 A | 12/1999 | Masao | | |
| 6,151,112 A | 11/2000 | Atkinson et al. | | |
| 6,600,560 B2 | 7/2003 | Mikkelsen et al. | | |
| 2003/0090669 A1 * | 5/2003 | Jung et al. | ...................... | 356/450 |

FOREIGN PATENT DOCUMENTS

| | | |
|---|---|---|
| JP | 10-160576 A | 6/1998 |
| JP | 2002-031510 A | 1/2002 |
| KR | 10-1999-0045315 A | 6/1999 |
| KR | 10-2004-0048405 A | 6/2004 |

* cited by examiner

*Primary Examiner* — Kara E Geisel
(74) *Attorney, Agent, or Firm* — Lee & Morse, P.C.

(57) ABSTRACT

A light focusing unit and a spectrum measuring apparatus having the same are provided. The light focusing unit includes a light source section configured to emit light, a light guiding section configured to guide the light emitted from the light source section along multiple parallel light incidence paths, and a light focusing section configured to direct the light from the guiding section to be incident on a test position of a sample at different incidence angles.

17 Claims, 6 Drawing Sheets

LIGHT FOCUSING UNIT AND SPECTRUM MEASURING APPARATUS HAVING THE SAME

BACKGROUND

1. Field

Example embodiments relate to a spectrum measuring apparatus. More particularly, example embodiments relate to a light focusing unit and a spectrum measuring apparatus having the same, capable of guiding polarized light to be incident on a sample at multiple incidence angles, and measuring both split-beam and arc-minute spectra of numerous wavelength bands at the incidence angles.

2. Description of Related Art

Semiconductor devices are fabricated by sequentially or selectively performing numerous unit processes, e.g., diffusion, deposition, ion implantation, exposure, cleaning, etc., on a substrate. For example, during fabrication of a semiconductor device, an ultra thin film having a thickness of several nanometers or less may be deposited on the substrate. A spectrum measuring apparatus, e.g., a spectroscopic ellipsometer, may be used to, e.g., precisely, measure the thickness of the ultra thin film and optical properties of a material of which the ultra thin film is formed.

Figure 1:
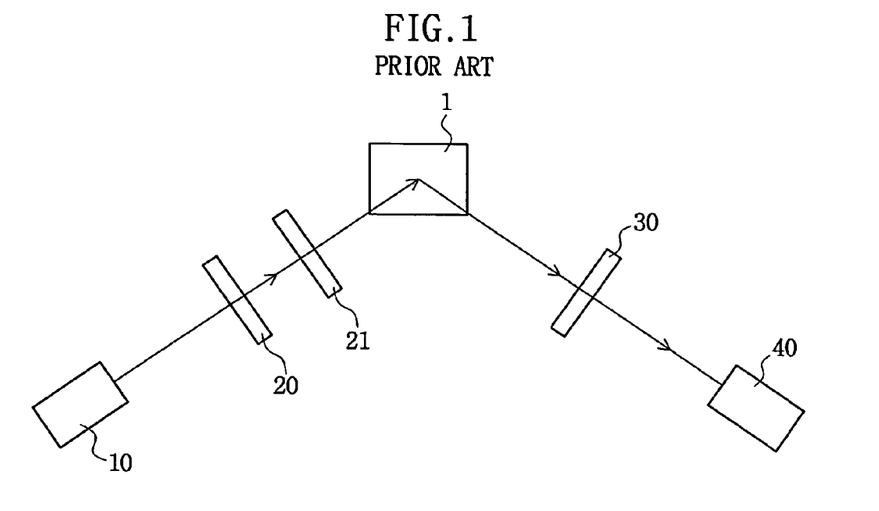
FIG. 1 illustrates a conventional spectrum measuring apparatus.

The spectroscopic ellipsometer determines complex refractive indices n and k using a pair of spectra $\Delta$ and $\Psi$ within an entire wavelength region measured at a single incidence angle. For example, as illustrated in FIG. 1, a conventional spectroscopic ellipsometer may include a light source section 10 emitting light, a polarized light generator 20 polarizing the light of the light source section 10 to cause the polarized light to be incident on a sample 1, a polarized light detecting section 30 detecting the polarized light reflected from the sample 1, and a detector 40 acquiring spectra from the detected polarized light. The spectroscopic ellipsometer may also include a compensator 21.

The conventional spectroscopic ellipsometer may be a single incidence-angle spectroscopic ellipsometer. However, the conventional single incidence-angle spectroscopic ellipsometer may have a low sensitivity to a vertical geometric structure of a thin film material, despite having a rapid measurement speed.

SUMMARY

Embodiments are therefore directed to a light focusing unit and a spectrum measuring apparatus having the same, which substantially overcome one or more of the problems due to the limitations and disadvantages of the related art.

It is therefore a feature of an embodiment to provide a light focusing unit and a spectrum measuring apparatus having the same, capable of guiding polarized light to be incident on a sample at multiple incidence angles.

It is therefore another feature of an embodiment to provide a light focusing unit and a spectrum measuring apparatus having the same, capable of measuring both split-beam and arc-minute spectra of numerous wavelength bands at incidence angles at which light is incident on a sample.

At least one of the above and other features and advantages may be realized by providing a light focusing unit, including a light source section configured to emit light, a light guiding section configured to guide the light emitted from the light source section along multiple parallel light incidence paths, and a light focusing section configured to cause the light guided along the light incidence paths to be incident on a test position of a sample at different incidence angles.

Here, the light guiding section may polarize the emitted light to the light focusing section. The light focusing section may include a focusing section body having a shape of a rod having a predetermined length, a first incidence plane part formed on one face of the focusing section body, and having a flat plane such that the light guided along the light incidence paths is incident; and a first emergence plane part formed on the other face of the focusing section body, and having a convex plane such that the light passing through the first incidence plane part and the focusing section body is guided at the different incidence angles. At this time, the focusing section body may include an axis that extends in a lengthwise direction and serves as a wavelength axis, and another axis that is perpendicular to the wavelength axis and serves as an incidence-angle axis.

At least one of the above and other features and advantages may also be realized by providing a spectrum measuring apparatus, including a light source section configured to emit light, a polarized light generator configured to polarize the light emitted from the light source section along multiple parallel light incidence paths, a light focusing section configured to cause the light guided along the light incidence paths to be incident on a test position of a sample at different incidence angles, a light collimating section configured to guide the light, which is focused on the test position of the sample and reflected at different emergence angles corresponding to the incidence angles, along multiple parallel light emergence paths, and a light detecting section configured to detect spectra from the light guided along the light emergence paths according to the different emergence angles.

Here, the light focusing section may include a focusing section body having a shape of a rod having a predetermined length, a first incidence plane part formed on one face of the focusing section body, and having a flat plane such that the light guided along the light incidence paths is incident, and a first emergence plane part formed on the other face of the focusing section body, and having a convex plane such that the light passing through the first incidence plane part and the focusing section body is guided at the different incidence angles.

Further, the light collimating section may include an collimating section body having a shape of a rod having a predetermined length, a second incidence plane part formed on one face of the emergence section body, and having a convex plane such that the light reflected from the sample to exit at the different emergence angles is incident; and a second emergence plane part formed on the other face of the emergence section body, and having a flat plane shape such that the light passing through the second incidence plane part and the collimating section body is guided to form the light emergence paths.

Also, each of the focusing section body and the collimating section body may include an axis that extends in a lengthwise direction and serves as a wavelength axis, and another axis that is perpendicular to the wavelength axis and serves as an incidence-angle axis. The light detecting section may include a charge coupled device (CCD) light detector, and the wavelength axis and the incidence-angle axis may be preset for the light detection section.

Further, the polarized light generator may be connected with a motor, which receives an electrical signal from the outside and generates a rotational force, and the motor may rotate the polarized light generator at a predetermined speed.

In addition, the first emergence plane part may be configured so that sub-parts having different curvature radii are detachably stacked, and the second incidence plane part may be configured so that sub-parts having different curvature radii are detachably stacked.

BRIEF DESCRIPTION OF THE DRAWINGS

The above and other features and advantages will become more apparent to those of ordinary skill in the art by describing in detail exemplary embodiments with reference to the attached drawings, in which.

DETAILED DESCRIPTION

Korean Patent Application No. 10-2009-0038399, filed on Apr. 30, 2009, in the Korean Intellectual Property Office, and entitled: "Light Focusing Unit and Spectrum Measuring Apparatus Having the Same," is incorporated by reference herein in its entirety.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the invention to those skilled in the art.

In the drawing figures, the dimensions of layers and regions may be exaggerated for clarity of illustration. It will also be understood that when a layer or element is referred to as being "on" another layer or substrate, it can be directly on the other element or substrate, or intervening elements may also be present. In addition, it will also be understood that when an element is referred to as being "between" two elements, it can be the element layer between the two elements, or one or more intervening elements may also be present. Like reference numerals refer to like elements throughout.

Figure 2:
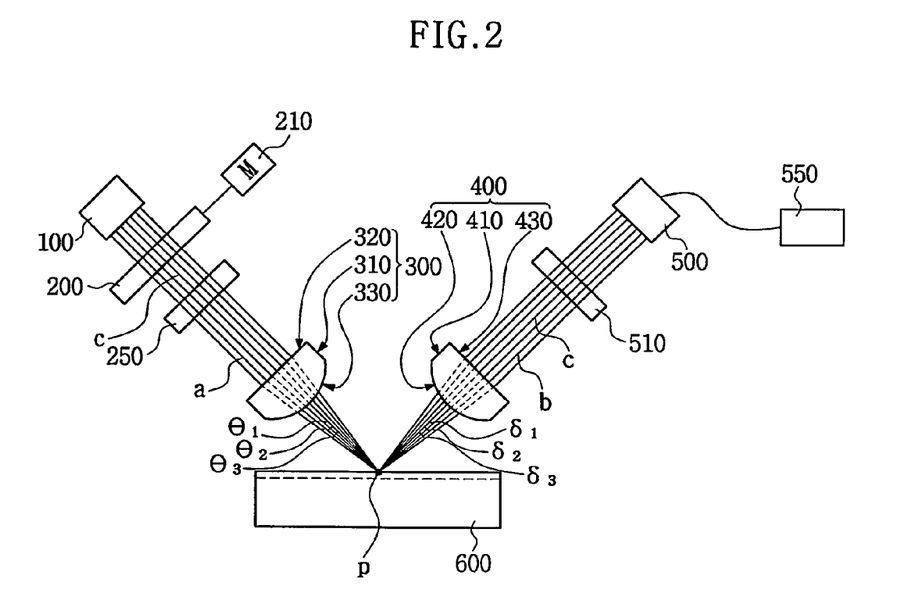
FIG. 2 illustrates a spectrum measuring apparatus according to an example embodiment.
Figure 3:
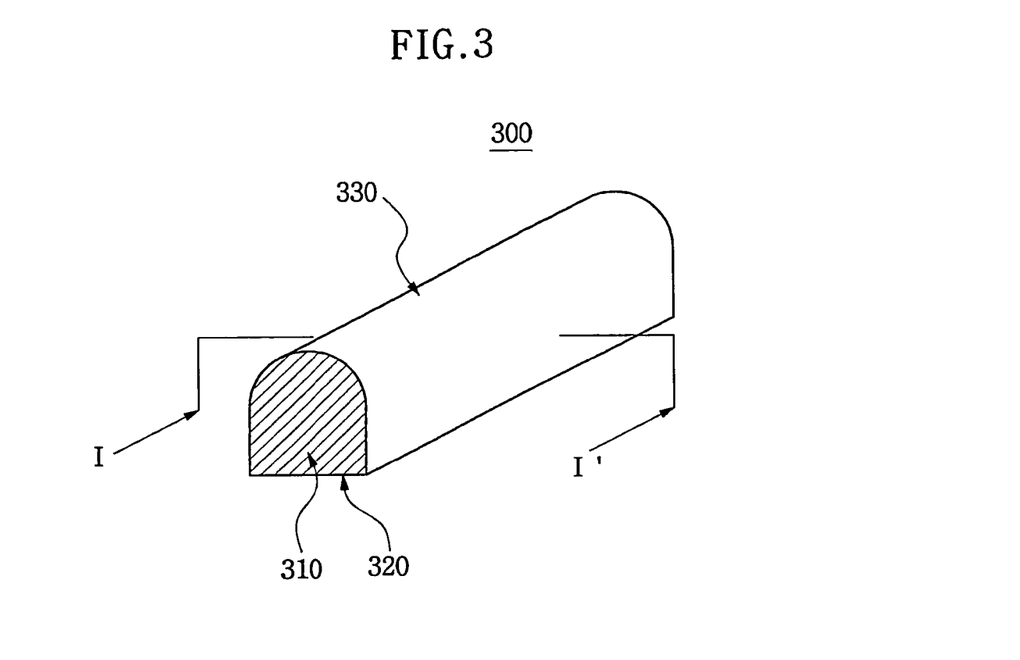
FIG. 3 illustrates a perspective view of a light focusing section in FIG. 2.
Figure 4:
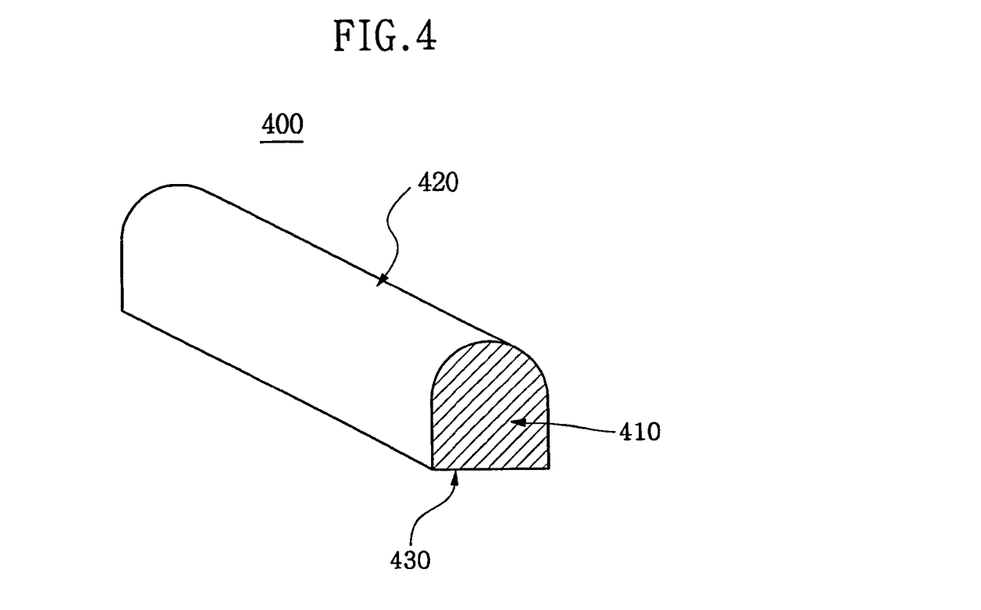
FIG. 4 illustrates a perspective view of a light collimating section in FIG. 2.
Figure 5:
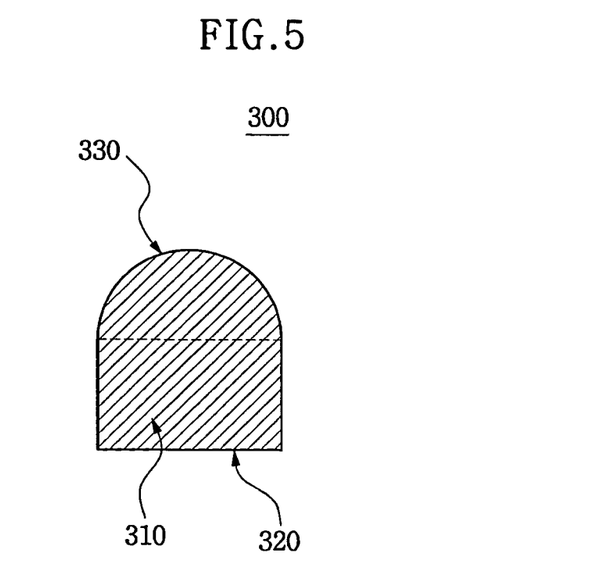
FIG. 5 illustrates a cross-sectional view taken along line I-I' of FIG. 3.

Reference will now be made to a light focusing unit and a spectrum measuring apparatus having the same according to an example embodiment with reference to FIGS. 2-5. FIG. 2 illustrates a spectrum measuring apparatus according to an example embodiment. FIG. 3 illustrates an enlarged perspective view of a light focusing section of FIG. 2. FIG. 4 illustrates an enlarged perspective view of a light collimating section of FIG. 2. FIG. 5 illustrates a cross-sectional view taken along line I-I' of FIG. 3.

A spectrum measuring apparatus according to an example embodiment may include a light focusing unit capable of guiding polarized light to be incident on a sample at multiple incidence angles. A configuration of the light focusing unit will be described below along with a configuration of the spectrum measuring apparatus.

Referring to FIG. 2, the spectrum measuring apparatus may include a light focusing unit, a light collimating section 400, and a light detecting section 500. The light focusing unit may include a light source section 100 emitting light, e.g., laser beams, a polarized light generator 200, and a light focusing section 300. The light source section 100 may emit collimated light.

The polarized light generator 200 may be installed adjacent to the light source section 100. The polarized light generator 200 polarizes the light emitted from the light source section 100, so the polarized light proceeds along a plurality of light incidence paths "a" that are parallel to one another. The polarized light generator 200 may not add the angles of the collimated light.

The light focusing section 300 may be installed adjacent to the polarized light generator 200, e.g., the polarized light generator 200 may be between the light source section 100 and the light focusing section 300. The light focusing section 300 may be positioned between the polarized light generator 200 and a sample 600, so the light focusing section 300 may focus the polarized light from the polarized light generator 200, i.e., light along the light incidence paths "a", on a test position P of the sample 600 at different incidence angles $\theta_1$, $\theta_2, \theta_3, \ldots, \theta_n$. For example, the sample 600 may be a silicon substrate.

The light collimating section 400 may be adjacent to the sample 600. The light collimating section 400 may collimate light, i.e., light reflected from the test position P of the sample 600, at different emergence angles $\delta_1, \delta_2, \delta_3, \ldots, \delta_n$, corresponding to the incidence angles $\theta_1, \theta_2, \theta_3, \ldots, \theta_n$, along a plurality of light emergence paths "b" that are parallel to one another. The light collimating section 400 may have a substantially same configuration as the light focusing section 300, as will be discussed in more detail below. The light collimating section 400 may be disposed at a position having a same level and same configuration as, e.g., symmetrical to, the light focusing section 300 with respect to the sample 600.

The light detecting section 500 may be adjacent to the light collimating section 400, e.g., the light collimating section 400 may be between the sample 600 and the light detecting section 500. The light detecting section 500 detects spectra of the light from the light collimating section 400, i.e., light guided from the light collimating section 400 along the light emergence paths "b" according to the different emergence angles $\delta_1, \delta_2, \delta_3, \ldots, \delta_n$. The light detecting section 500 may be a polarized light detecting section. For example, the light detecting section 500 may include a charge coupled device (CCD) light detector, and may be configured to pre-set a wavelength axis and an incidence-angle axis.

In addition, both the polarized light generator 200 and the light detecting section 500 may include a polarizer (not shown). For example, the polarizer of the polarized light generator 200 may be rotated at a predetermined speed by a motor 210. The motor 210 receives an electrical signal from the outside, and generates a rotational force, so that it can rotate the polarizer at a predetermined speed. In another example, the polarizer of the light detecting section 500 may be rotated at a predetermined speed by a motor 550. Further, the polarized light generator 200 and the light detecting section 500 may include first and second compensators 250 and 510, respectively.

Next, a configuration of the light focusing section 300 mentioned above will be described in greater detail below with reference to FIGS. 3 and 5.

Referring to FIGS. 2-3 and 5, the light focusing section 300 may include a focusing section body 310, a first incidence plane part 320 formed on one face, i.e. a top face, of the focusing section body 310, and a first emergence plane part 330 formed on the other face, i.e. a bottom face, of the focusing section body 310. For example, the light focusing section 300 may be a spherical lens or a non-spherical lens, i.e., an aspherical lens.

The focusing section body 310 may be a plano-convex cylindrical lens, e.g., having a shape of a rod, with a predetermined length and a plano-convex cross section. An axis extending in a lengthwise direction of the focusing section body 310 may function as a wavelength axis. Thus, another axis perpendicular to the wavelength axis of the focusing section body 310 may function as an incidence-angle axis. In other words, the wavelength axis extends in an x-axial direction, whereas the incidence-angle axis extends in a y-axial direction.

The first incidence plane part 320 may include a substantially flat surface, and may face the polarized light generator 200. Therefore, light along the light incidence paths "a" from the polarized light generator 200 may be incident on the flat surface of the first incidence plane part 320 of the focusing section body 310 to be incident on the test position P of the sample 600.

The first emergence plane part 330 may be opposite the first incidence plane part 320. The first emergence plane part 330 may include a convex surface, e.g., a downwardly convex plane facing the sample 600, such that the light passing through the first incidence plane part 320 and the focusing section body 310 may be collimated at the different incidence angles $\theta_1, \theta_2, \theta_3, \ldots, \theta_n$ through the first emergence plane part 330 toward the sample 600.

Next, a configuration of the light collimating section 400 mentioned above will be described in greater detail below with reference to FIG. 4.

Referring to FIGS. 2 and 4, the light collimating section 400 may include a collimating section body 410 that may be a plano-convex cylindrical lens, e.g., having a shape of a rod with a predetermined length, a second incidence plane part 420 formed on one face, i.e. a bottom face, of the collimating section body 410, and a second emergence plane part 430 formed on the other face, i.e. a top face, of the collimating section body 410. The second incidence plane part 420 may have a convex plane facing the sample 600, so light reflected from the sample 600 at the different emergence angles $\delta_1, \delta_2, \delta_3, \ldots, \delta_n$ toward the light collimating section 400 may be incident on the second incidence plane part 420. The second emergence plane part 430 may have a flat plane opposite the second incidence plane part 420, such that light passing through the second incidence plane part 420 and the collimating section body 410 may pass through the second emergence plane part 430 to form the light emergence paths "b". For example, structures of the light focusing section 300 and the light collimating section 400 may be symmetrical, e.g., the first emergence plane part 330 and the second incidence plane part 420 may have same radii curvature.

The collimating section body 410 may have a shape of a rod having a predetermined length and a plano-convex cross section. Here, an axis extending in a lengthwise direction of the collimating section body 410 may function as a wavelength axis. Thus, another axis perpendicular to the wavelength axis of the collimating section body 410 may function as an incidence-angle axis. In other words, the wavelength axis extends in an x-axial direction, whereas the incidence-angle axis extends in a y-axial direction.

Figure 6:
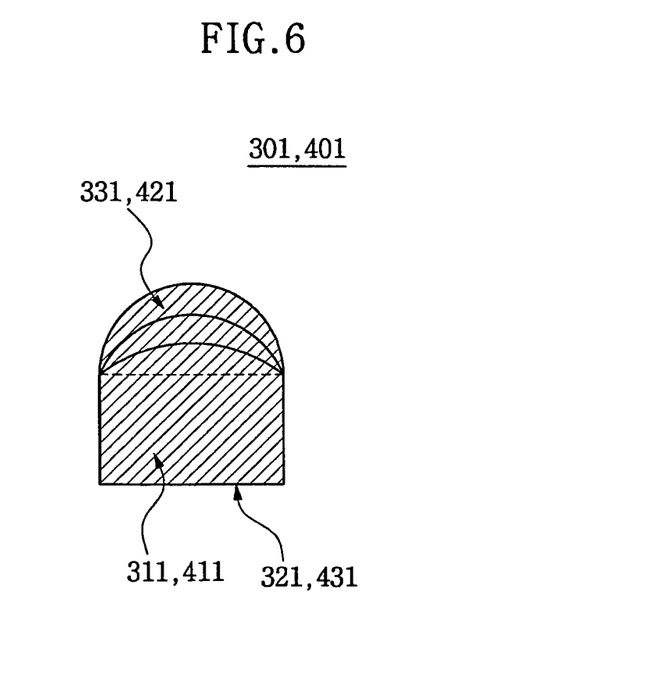
FIG. 6 illustrates a cross-sectional view of a light focusing section or a light collimating section according to another example embodiment.
Figure 7:
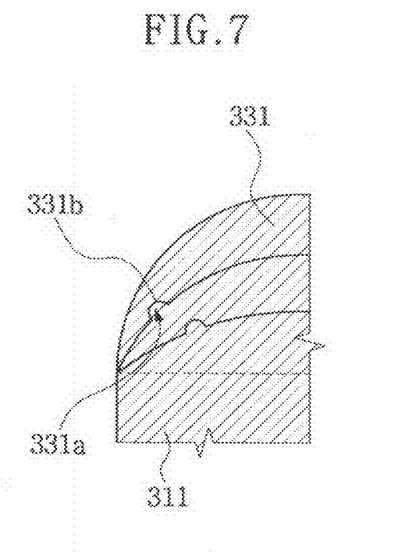
FIG. 7 illustrates a partial enlarged cross-sectional view of the light collimating section in FIG. 6.

FIG. 6 illustrates a cross-sectional view of another example of a light focusing section or a light collimating section according to an example embodiment. FIG. 7 illustrates a partial enlarged cross-sectional view of FIG. 6.

According to another embodiment, as illustrated in FIGS. 6-7, the spectrum measuring apparatus may include a light focusing section 301 and a light collimating section 401. A first emergence plane part 331 in the light focusing section 301 may be configured so that sub-parts having different curvature radii are detachably stacked. Further, a second incidence plane part 421 in the light collimating section 401 may be configured so that sub-parts having different curvature radii are detachably stacked. Here, among the reference numbers that have not yet been described, 311 indicates a focusing section body, 321 indicates a first incidence plane part, 411 indicates an emergence section body, and 421 indicates a second emergence plane part.

Next, an operation of the spectrum measuring apparatus in FIG. 2 will be described.

Referring to FIG. 2, the light source section 100 may emit light, e.g., laser beams. The emitted light may be incident on the polarized light generator 200, so the polarized light generator 200 may polarize the emitted light to be guided along the light incidence paths "a" that are parallel to one another. The polarized light may be guided from the polarized light generator 200 to be incident on the light focusing section 300.

In detail, the polarized light may be incident on the first incidence plane part 320 of the focusing section body 310, e.g., the incidence angle of the polarized light on the first incidence plane part 320 may be 90°. In this manner, the light incident on the first incidence plane part 320 passes through the focusing section body 310 and the first emergence plane part 330 formed on the bottom face of the focusing section body 310 in a convex shape.

Here, the Y axis extending in the lengthwise direction of the focusing section body 310 functions as a wavelength axis (or a split-beam axis), whereas the X axis perpendicular to the wavelength axis functions as an incidence-angle axis (or an arc-minute axis).

Then, the light passing through the first emergence plane part 330 is focused onto the test position P of the sample 600. Thus, referring to FIG. 2, the light passing through the first emergence plane part 330 is incident on the test position P of the sample 600 at different incidence angles $\theta_1, \theta_2, \theta_3, \ldots, \theta_n$ with respect to an optical axis c. As a result, the light passing through the first emergence plane part 330 can be focused onto the test position P of the sample 600.

In this manner, the light reflected from the test position P of the sample 600 may travel toward the light collimating section 400 at different emergence angles $\delta_1, \delta_2, \delta_3, \ldots, \delta_n$ which have substantially the same angles as respective incidence angles $\theta_1, \theta_2, \theta_3, \ldots, \theta_n$. In detail, the light reflected from the test position P of the sample 600 at the different emergence angles $\delta_1, \delta_2, \delta_3, \ldots, \delta_n$ may be incident on the convex second incidence plane part 420 of the light collimating section 400.

The light having the different emergence angles $\delta_1, \delta_2, \delta_3, \ldots, \delta_n$ may pass through the rod-shaped collimating section body 410 of the light collimating section 400, and then through the flat second emergence plane part 430 of the collimating section body 410. Thus, the light having the different emergence angles $\delta_1, \delta_2, \delta_3, \ldots, \delta_n$ may pass through the second emergence plane part 430 of the collimating section body 410, and may be detected at the numerous parallel light emergence paths "b" by the light detecting section 500.

Figure 8:
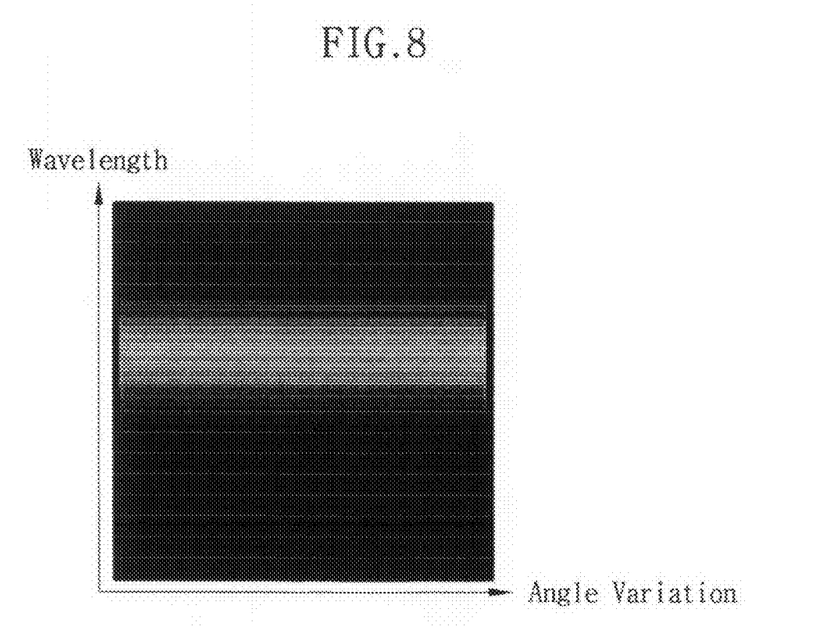
FIG. 8 illustrates a graph showing an example of a signal based on a wavelength axis and an incidence-angle axis preset for a light detecting section according to an example embodiment.

Here, the light detecting section 500 may be a CCD light detector. Since the wavelength axis (or split-beam axis) and the incidence-angle axis (or arc-minute axis) are preset for the light detection section 500, the light detection section 500 may acquire split-beam spectra at the incidence angles $\theta_1, \theta_2, \theta_3, \ldots, \theta_n$, at which the light is incident on the sample 600. For example, the CCD light detector having 1024×1024 pixels may acquire split-beam spectra at maximum 1024 incidence angles. This may be regarded as the CCD light detector acquiring arc-minute spectra at 1024 wavelengths. FIG. 8 illustrates a graph showing an example of a signal based on a wavelength axis and an incidence-angle axis preset for the light detecting section 500.

Figure 9A:
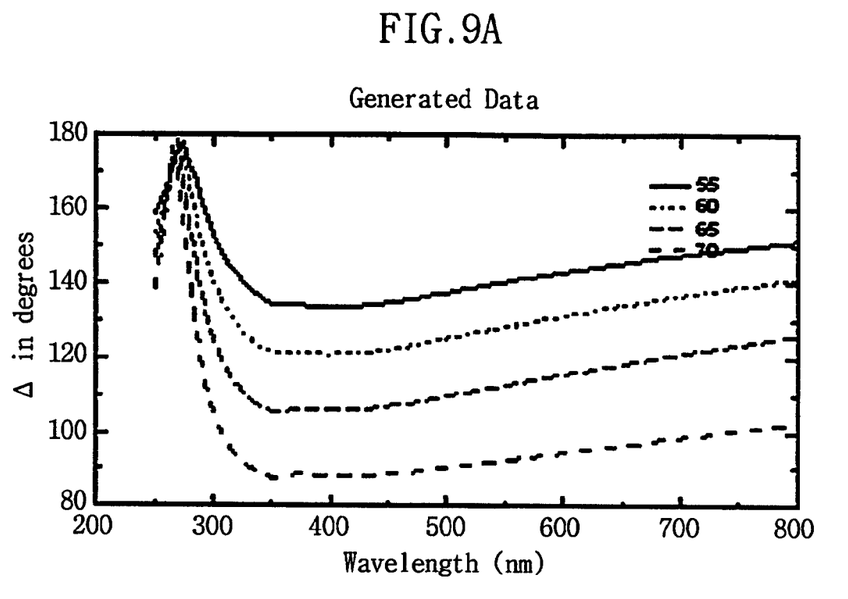
FIGS. 9A and 9B illustrate graphs showing split-beam spectra acquired depending on a variety of incidence angles using a spectrum measuring apparatus according to an example embodiment.
Figure 9B:
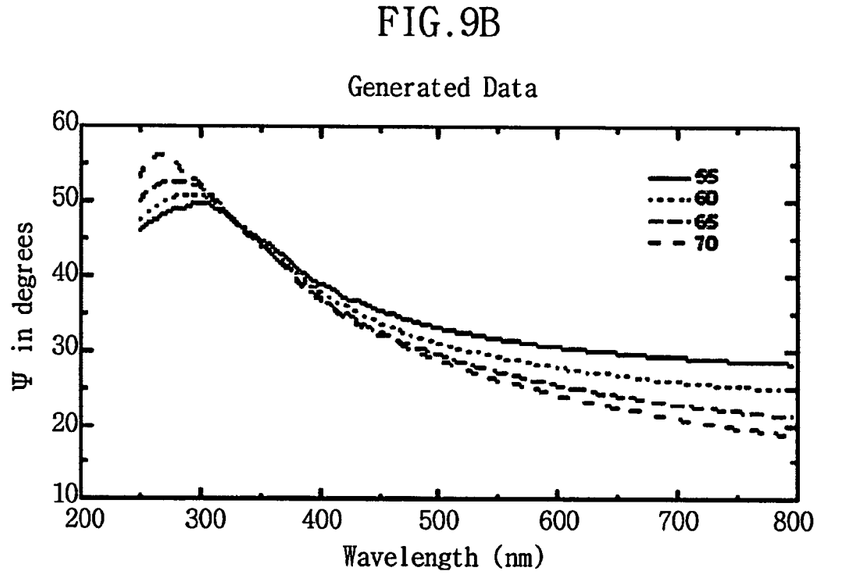
Figure 10A:
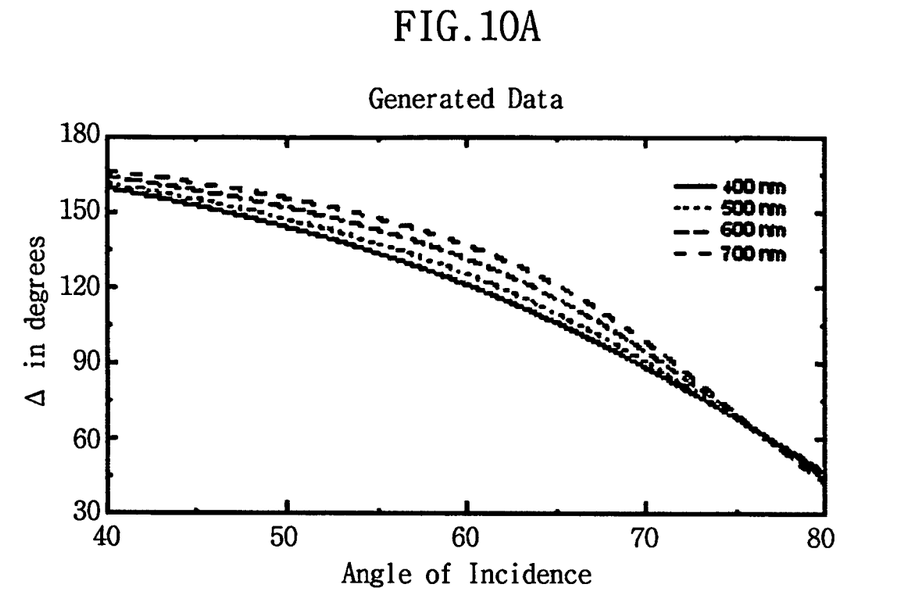
FIGS. 10A and 10B illustrate graphs showing split-beam spectra acquired depending on a variety of wavelengths using a spectrum measuring apparatus according to an example embodiment.
Figure 10B:
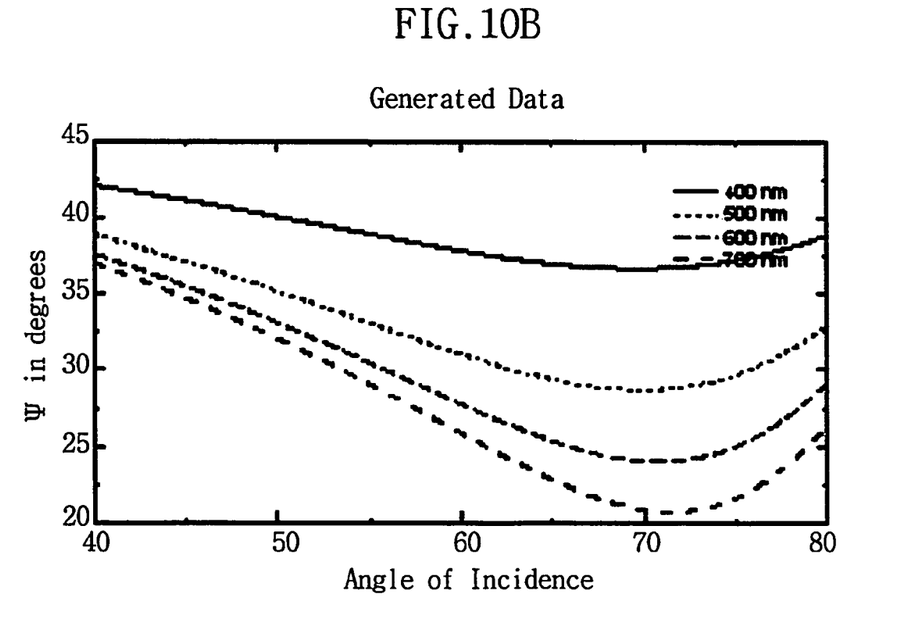

FIGS. 9A and 9B are graphs showing split-beam spectra acquired depending on a variety of incidence angles using a spectrum measuring apparatus according to an example embodiment. FIGS. 10A and 10B are graphs showing split-beam spectra acquired depending on a variety of wavelengths using a spectrum measuring apparatus according to an example embodiment.

In detail, FIGS. 9A and 9B show the split-beam spectra acquired when the light is irradiated onto the sample 600, which is a silicon substrate where an oxide layer ($SiO_2$) is grown at a thickness of 50 nm, at incidence angles of 55°, 60°, 65°, and 70°. Further, FIGS. 10A and 10B show the arc-minute spectra acquired when the light is irradiated onto the sample 600 at wavelengths of 400 nm, 500 nm, 600 nm, and 700 nm. Thus, the spectrum measuring apparatus according to example embodiments may measure both the split-beam spectra and the arc-minute spectra, as shown in FIGS. 9A through 10B.

An operation of the spectrum measuring apparatus in FIGS. 6-7 is as follows. Referring to FIGS. 6-7, the incidence angles at which the light is incident on the sample 600 may be adjusted at various intervals.

More specifically, in the case of the light focusing section 301, the first incidence plane part 331 formed on the top face of the focusing section body 311 of the light focusing section 301 may be configured so that multiple sub-parts having different curvature radii are detachably stacked. Here, the curvature radii of the multiple sub-parts constituting the first incidence plane part 331 may be gradually increased or decreased in proportion to the distance from the focusing section body 311.

Similarly, in the case of the light collimating section 401, the first emergence plane part 421 formed on the top face of the collimating section body 411 of the light collimating section 401 may be configured so that multiple sub-parts having different curvature radii are detachably stacked. Here, the curvature radii of the multiple sub-parts constituting the first emergence plane part 421 may be gradually increased or decreased in proportion to the distance from the collimating section body 411.

Alternatively or additionally, as illustrated in FIG. 7, the detachable stacking may employ a slidable coupling mechanism. For example, at least one sliding rail 331a may be slidably fitted into at least one sliding groove 331b, such that the multiple sub-parts constituting the first incidence plane part 331 are closely contacted with one other. The detachable stacking may employ the above-mentioned slidable coupling mechanism in the collimating section body 411 as well.

Thus, when the light focusing section 301 and the light collimating section 401 shown in FIGS. 6 and 7 are used, one of the first incidence plane part 331 and the second emergence plane part 421 may be used. Thereby, the intervals of the incidence angles at which the light is incident on the test position P of the sample 600 may be variously adjusted.

As described above, the inventive concept is capable of guiding light, which is polarized after being emitted from a light source, to be incident on a sample at multiple incidence angles. Further, the inventive concept is capable of measuring both the split-beam and arc-minute spectra of numerous wavelength bands at incidence angles at which the light is incident on the sample. Therefore, a spectrum measuring apparatus according to example embodiments may be sensitive to both a geometrical difference and an optical property resulting from a vertical structure of the substrate that is a target of measurement, while having reduced operating/measuring time.

In contrast, a conventional variable incidence-angle spectroscopic ellipsometer, i.e., a structure including a goniometer that varies an incidence angle at which light is incident on a substrate as a sample, may require an auxiliary hardware operation of the goniometer for varying the incidence angle at which the light is incident on the sample. As such, an operating time of the goniometer and a measuring time including spectrum acquisition in the conventional variable incidence-angle spectroscopic ellipsometer may be increased in proportion to a number of variable incidence angles. Also, a conventional focused-beam ellipsometer, i.e., an ellipsometer in which an incidence angle is diversified using typical lenses, uses a single wavelength, and thus may require a multi-wavelength laser or a filter capable of selecting a desired wavelength in order to acquire a multi-wavelength spectrum. As such, the conventional focused-beam ellipsometer may have problems with a limitation on wavelength selection and a delay of the measurement speed in proportion to a number of selected wavelengths.

Exemplary embodiments have been disclosed herein, and although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. A light focusing unit, comprising:
   a light source section configured to emit light;
   a light guiding section configured to guide the light emitted from the light source section along multiple parallel light incidence paths; and
   a light focusing section configured to direct the light from the guiding section to be incident on a test position of a sample at different incidence angles, the light focusing section including:
   a focusing section body having a shape of a rod, the rod having a predetermined width along a first direction and a predetermined length along a second direction perpendicular to the first direction, the predetermined length of the rod being larger than the predetermined width of the rod,
   a first incidence plane part with a substantially flat surface on the focusing section body, and
   a first emergence plane part with a convex surface on the focusing section body opposite the first incidence plane part, a distance between the first incidence plane part and the first emergence plane part being defined along a third direction substantially perpendicular to each of the first and second directions, and the first emergence plane part having a plurality of sub-parts having different curvature radii and being detachably stacked.

2. The light focusing unit as claimed in claim 1, wherein the light guiding section is configured to polarize the light emitted from the light source, such that light incident on the light focusing section is polarized.

3. The light focusing unit as claimed in claim 1, wherein the focusing section body is a plano-convex cylindrical lens.

4. The light focusing unit as claimed in claim 1, wherein the flat surface of the first incidence plane part faces the light guiding section, and the convex surface of the first emergence plane part faces the sample.

5. The light focusing unit as claimed in claim 1, wherein the focusing section body includes a wavelength axis along the second direction and an incidence-angle axis along the third direction perpendicular to the wavelength axis, the light from the guiding section being incident on the focusing section body in a plane defined by the second and third directions.

6. A spectrum measuring apparatus, comprising:
a light source section configured to emit light;
a light guiding section configured to guide the light emitted from the light source section along multiple parallel light incidence paths;
a light focusing section configured to direct the light from the guiding section to be incident on a test position of a sample at different incidence angles, the light focusing section including a plano-convex cylindrical lens, the plano-convex cylindrical lens including:
a focusing section body having a shape of a rod with a predetermined length,
a first incidence plane part on the focusing section body, the first incidence plane part including a substantially flat surface, and
a first emergence plane part on the focusing section body, the first emergence plane part including a convex surface;
a light collimating section configured to guide light reflected from the test position at different emergence angles corresponding to the different incidence angles along multiple parallel light emergence paths, the light collimating section including:
a collimating section body having a shape of a rod with a predetermined length,
a second incidence plane part on the emergence section body, the second incidence plane part including a convex surface, and
a second emergence plane part on the collimating section body opposite the second incidence plane part, the second emergence plane part including a substantially flat surface; and
a light detecting section configured to detect spectra from the light guided by the light collimating section.

7. The spectrum measuring apparatus as claimed in claim 6, wherein the first emergence plane part includes a plurality of sub-parts having different curvature radii, the plurality of sub-parts being detachably stacked.

8. The spectrum measuring apparatus as claimed in claim 6, wherein the second incidence plane part includes a plurality of sub-parts having different curvature radii, the plurality of sub-parts being detachably stacked.

9. The spectrum measuring apparatus as claimed in claim 6, wherein each of the focusing and emergence section bodies includes a wavelength axis along a first direction and an incidence-angle axis along a second direction perpendicular to the wavelength axis, a distance between each incidence plane part and a respective emergence plane part being defined along the second direction, and a length of each of the focusing and emergence section bodies being longer along the first direction than in a third direction perpendicular to each of the first and second directions.

10. The spectrum measuring apparatus as claimed in claim 9, wherein the light detecting section includes a charge coupled device (CCD) light detector, and the wavelength axes and the incidence-angle axes are preset for the light detection section.

11. The spectrum measuring apparatus as claimed in claim 6, wherein the light guiding section includes a polarized light generator connected with a motor, the motor being configured to receive an electrical signal from the outside, to generate a rotational force, and to rotate the polarized light generator at a predetermined speed.

12. The spectrum measuring apparatus as claimed in claim 6, wherein the light focusing section and light collimating section are positioned symmetrically with respect to the test position.

13. The light focusing unit as claimed in claim 1, wherein the light focusing section consists essentially of a single focusing section body.

14. The light focusing unit as claimed in claim 13, wherein the single focusing section body is a plano-convex cylindrical lens.

15. The spectrum measuring apparatus as claimed in claim 6, wherein the plano-convex cylindrical lens of the light focusing section includes a plurality of sub-parts having different convex radii.

16. A light focusing unit, comprising:
a light source section configured to emit light;
a light guiding section configured to guide the light emitted from the light source section along multiple parallel light incidence paths; and
a light focusing section configured to direct the light from the guiding section to be incident on a test position of a sample at different incidence angles, the light focusing section including a plano-convex cylindrical lens with a plurality of sub-parts having different convex radii.

17. The light focusing unit as claimed in claim 16, wherein sizes of the convex radii of the sub-parts are proportional to a distance from the focusing section body.

* * * * *